US008403850B2

(12) United States Patent
Varghese et al.

(10) Patent No.: US 8,403,850 B2
(45) Date of Patent: Mar. 26, 2013

(54) RAPID TWO/THREE-DIMENSIONAL SECTOR STRAIN IMAGING

(75) Inventors: Tomy Varghese, Madison, WI (US); Hao Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 917 days.

(21) Appl. No.: 12/054,830

(22) Filed: Mar. 25, 2008

(65) Prior Publication Data
US 2009/0247871 A1 Oct. 1, 2009

(51) Int. Cl.
*A61B 8/00* (2006.01)

(52) U.S. Cl. ......... 600/438; 600/449; 600/443; 382/128

(58) Field of Classification Search ............ 600/437, 600/420, 438, 450, 443; 382/128
See application file for complete search history.

(56) References Cited

U.S. PATENT DOCUMENTS

| | | | |
|---|---|---|---|
| 6,270,459 B1 * | 8/2001 | Konofagou et al. | 600/449 |
| 6,277,074 B1 | 8/2001 | Chaturvedi et al. | |
| 6,475,146 B1 * | 11/2002 | Frelburger et al. | 600/437 |
| 6,494,834 B2 * | 12/2002 | Konofagou et al. | 600/438 |
| 6,508,768 B1 * | 1/2003 | Hall et al. | 600/443 |
| 6,511,427 B1 * | 1/2003 | Sliwa et al. | 600/438 |
| 6,517,485 B2 * | 2/2003 | Torp et al. | 600/438 |
| 6,520,913 B1 * | 2/2003 | Pesavento et al. | 600/438 |
| 6,569,098 B2 * | 5/2003 | Kawchuk | 600/437 |
| 6,749,571 B2 * | 6/2004 | Varghese et al. | 600/450 |
| 6,776,759 B2 * | 8/2004 | Heimdal et al. | 600/442 |
| 6,969,352 B2 * | 11/2005 | Chiang et al. | 600/437 |
| 7,050,610 B2 * | 5/2006 | Chen et al. | 382/128 |
| 7,077,807 B2 * | 7/2006 | Torp et al. | 600/438 |
| 7,115,093 B2 * | 10/2006 | Halmann et al. | 600/437 |
| 7,166,075 B2 * | 1/2007 | Varghese et al. | 600/439 |
| 7,244,230 B2 * | 7/2007 | Duggirala et al. | 600/300 |
| 7,275,439 B2 | 10/2007 | Zagzebski et al. | |
| 7,297,116 B2 | 11/2007 | Varghese et al. | |
| 7,331,926 B2 | 2/2008 | Varghese et al. | |
| 7,766,836 B2 * | 8/2010 | Waki | 600/443 |
| 7,803,113 B2 * | 9/2010 | Houle et al. | 600/443 |
| 7,819,824 B2 * | 10/2010 | Sarvazyan et al. | 600/587 |
| 7,828,731 B2 * | 11/2010 | Baba et al. | 600/437 |
| 7,828,733 B2 * | 11/2010 | Zhang et al. | 600/437 |
| 2003/0171672 A1 * | 9/2003 | Varghese et al. | 600/420 |
| 2004/0015079 A1 * | 1/2004 | Berger et al. | 600/437 |
| 2004/0059224 A1 * | 3/2004 | Varghese et al. | 600/450 |
| 2004/0127790 A1 * | 7/2004 | Lang et al. | 600/438 |
| 2004/0147840 A1 * | 7/2004 | Duggirala et al. | 600/437 |
| 2004/0210136 A1 * | 10/2004 | Varghese et al. | 600/443 |
| 2004/0215075 A1 * | 10/2004 | Zagzebski et al. | 600/442 |
| 2005/0015009 A1 * | 1/2005 | Mourad et al. | 600/438 |
| 2005/0119568 A1 * | 6/2005 | Salcudean et al. | 600/437 |
| 2005/0165309 A1 * | 7/2005 | Varghese et al. | 600/449 |
| 2005/0251042 A1 * | 11/2005 | Sandrin et al. | 600/443 |
| 2005/0283076 A1 * | 12/2005 | Hangiandreou et al. | 600/443 |
| 2006/0079773 A1 * | 4/2006 | Mourad et al. | 600/438 |
| 2006/0173319 A1 * | 8/2006 | Sumi | 600/437 |
| 2006/0184025 A1 * | 8/2006 | Sumi | 600/438 |
| 2006/0285731 A1 | 12/2006 | Jiang et al. | |
| 2007/0016031 A1 * | 1/2007 | Mourad et al. | 600/437 |

(Continued)

*Primary Examiner* — Brian Casler
*Assistant Examiner* — Serkan Akar
(74) *Attorney, Agent, or Firm* — Boyle Fredrickson S.C.

(57) ABSTRACT

An elastographic imaging system providing for axial, lateral and elevational strain measurements employs a series of one-dimensional axial measurements to deduce a coarse axial, lateral and/or elevational displacement that is used to guide one or more, two- or three-dimensional cross-correlations of smaller kernels providing improved image resolution.

25 Claims, 4 Drawing Sheets

U.S. PATENT DOCUMENTS

| | | |
|---|---|---|
| 2007/0043597 A1* | 2/2007 | Donaldson .................... 705/3 |
| 2007/0083113 A1* | 4/2007 | Varghese et al. ............. 600/437 |
| 2007/0083120 A1 | 4/2007 | Cain et al. |
| 2007/0234806 A1 | 10/2007 | Jiang et al. |
| 2007/0238998 A1* | 10/2007 | Nycz et al. .................... 600/437 |
| 2009/0247871 A1* | 10/2009 | Varghese et al. ............. 600/438 |
| 2009/0312638 A1* | 12/2009 | Bartlett ........................ 600/443 |
| 2010/0022882 A1* | 1/2010 | Duckworth et al. .......... 600/447 |

* cited by examiner

FIG. 8

RAPID TWO/THREE-DIMENSIONAL SECTOR STRAIN IMAGING

STATEMENT REGARDING FEDERALLY SPONSORED RESEARCH OR DEVELOPMENT

This invention was made with United States government support awarded by the following agencies:
NIH EB003853
The United States government has certain rights in this invention.

CROSS-REFERENCE TO RELATED APPLICATIONS

BACKGROUND OF THE INVENTION

The present invention relates to ultrasonic imaging and in particular to an apparatus and method for making ultrasonic strain measurements providing both axial, lateral and elevational strain for imaging with a sector or phased-array geometry with 1-D or 2-D transducers.

Elastography is an imaging modality that reveals the stiffness properties of tissue, for example, axial displacement, lateral displacement, elevational displacement, axial strain, lateral strain, elevational strain, Poisson's ratio, Young's modulus and other common strain and strain-related measurements. Strain measurements over an area may be mapped to a grey or color scale to form a strain "image."

In quasi-static elastography, two images of tissue to be measured (a "pre-compression" and "post-compression" image) are obtained, typically by an ultrasound device, with the tissue in two different states of compression, for example, no compression and a given positive or negative (tensile) compression. Tissue may be compressed by an external agency such as a probe or the like, or by muscular action or movement of organs near the tissue.

Strain is deduced from these two images by computing gradients of the relative local shifts or displacement in the images along the compression axis. Quasi-static elastography is analogous to a physician's palpation of tissue in which the physician identifies firm structures by pressing the tissue and detecting the amount the tissue yields under this pressure.

Determining the relative displacement of tissue between the pre- and post-compression images may be done by analyzing portions of the ultrasonic images along a series of one-dimensional kernels normally extending along the axis of compression. The signal in each kernel in the pre-compression image is cross-correlated to the signal in a search area of the post-compression image. This cross-correlation process is repeated for many kernels in the pre-compression image yielding local displacement of tissue for each kernel. The gradient of these local displacements yields a measure of the local strains in the tissue.

The use of smaller kernels in this cross-correlation process can provide for improved image resolution. Yet if there are large displacements in the tissue, small kernels are subject to statistical miscorrelations leading to erroneous displacement results. In contrast, larger kernels provide more robust correlations over large search areas but can decrease the resolution of the image and can greatly increase the computational time.

U.S. patent application Ser. No. 11/384,607, filed Mar. 20, 2006, assigned to the same assignee as the present invention and hereby incorporated by reference, discloses a technique capturing the benefits of both small and large kernels through a multistep process where a larger kernel (typically with reduced sampling resolution) is used to obtain a coarse displacement map which is then used to guide the placement of small kernels to obtain a fine displacement map of high accuracy.

In two-dimensional elastography, strain is determined both in an axial direction aligned with the direction of compression and a lateral direction perpendicular to the direction of compression. The kernels in this case are two-dimensional and thus encompass greater amounts of data and must be cross-correlated in two dimensions. These factors significantly increase the computational burden of two-dimensional elastography.

In three-dimensional elastography, strain is determined both in an axial direction aligned with the direction of compression and lateral and elevational directions perpendicular to the direction of compression. The kernels in this case are three-dimensional and thus encompass greater amounts of data and must be cross-correlated in three dimensions. These factors significantly increase the computational burden of three-dimensional elastography.

Further complicating two and three-dimensional elastography, in many ultrasonic scanning systems the ultrasonic beam spreads outward in a fan beam. This requires that the kernels be sector shaped with the sector dimensions changing depending on the location in the imaged object and the amount of compression. The sector shape increases the complexity of two and three-dimensional cross-correlation over a larger area kernel.

BRIEF SUMMARY OF THE INVENTION

The present inventors have determined that a good approximation of axial, lateral and elevational displacement of tissue can be obtained by taking a series of laterally and/or elevationally displaced one-dimensional axial correlations. The lateral and/or elevational displacement of the tissue is approximated by the lateral and/or elevational location of the axial correlation having the highest peak. The peak of that axial correlation approximates the axial displacement of the tissue. This approximation may be used to guide a cross-correlation using compact two and three-dimensional kernels to obtain a fine grain displacement measurement.

Specifically, the present invention provides a method of two and three-dimensional strain imaging that starts by obtaining a pre-compression and post-compression ultrasonic data set of an imaged object composed of measurements along multiple axial lines through the imaged object. For each axial line and for each depth along each line, measurements of the axial line at a range of depths in the pre-compression ultrasonic data set are correlated against a corresponding axial line and laterally and/or elevationally adjacent axial lines in the post-compression ultrasonic data set. One line having maximum correlation is identified and the axial, lateral and elevational location of that maximum is marked as a line peak. A local area or volume correlation is then performed between the pre-compression and post-compression ultrasonic data setsoat points about the line peak to determine a subsample peak. The subsample peak provides a fine resolution axial, lateral and/or elevational displacement. Strain data based on these fine resolution axial, lateral and/or elevational displacements at a plurality of locations in the imaged object is then displayed.

It is thus one object of an embodiment of the invention to provide a rapid method of identifying axial, lateral and elevational displacement to guide a subsequent cross-correlation with small kernels to produce high-resolution two or three-dimensional displacement measurements.

The multiple axial lines of the ultrasonic data may diverge through the imaged object and the local area correlation may be performed on a sector grid conforming to the divergence of the axial lines in the vicinity of the line peak.

It is thus an object of an embodiment of the invention to provide a method that efficiently works with sector and phased array imaging common in many ultrasound machines.

The pre-compression and post-compression data may be normalized before processing.

It is thus an object of an embodiment of the invention to preprocess the raw ultrasonic data to improve the information obtained from a correlation process.

The one, two or three-dimensional correlation may be performed on B-mode data.

It is thus an object of an embodiment of the invention to make use of lower resolution B-mode data for the initial displacement determination to further speed this process.

The invention may further perform a first local area or volume correlation between the pre-compression and post-compression ultrasonic data sets at points about the line peak to determine a "coarse" subsample peak; and a second local area or volume correlation between the pre-compression and post-compression ultrasonic data sets at points about the coarse subsample peak to determine a finer subsample peak, the finer subsample peak providing improved resolution over the coarse subsample peak.

It is thus an object of an embodiment of the invention to permit multiple steps of two or three-dimensional correlation to more flexibly benefit from the trade-offs between large and small kernels in terms of processing speed and resolution.

The coarse subsample peak may use B-mode data for the local area or volume correlation and the subsample peak may use radio frequency (RF) data for the local area correlation.

It is thus an object of an embodiment of the invention to make use of the readily available high and low bandwidth signals in an ultrasound machine for the coarse and fine displacement measurements.

The number of laterally and elevationally adjacent lines examined may vary according to the relative change in peak correlation with respect to the previous peak correlation.

It is thus an object of an embodiment of the invention to further reduce the number of lines that must be analyzed for the coarse displacement determination.

At least one laterally and/or elevationally adjacent line may be an interpolated line between measurements of two axial lines. An interpolated line may be generated when an axial line of the two axial lines that is furthest from the corresponding line has a maximum correlation that has decreased by a predetermined amount.

It is thus an object of an embodiment of the invention to selectively boost the resolution of the coarse displacement determination in the lateral and/or elevational direction by selective interpolation.

These particular objects and advantages may apply to only some embodiments falling within the claims, and thus do not define the scope of the invention.

DETAILED DESCRIPTION OF THE INVENTION

Figure 1:
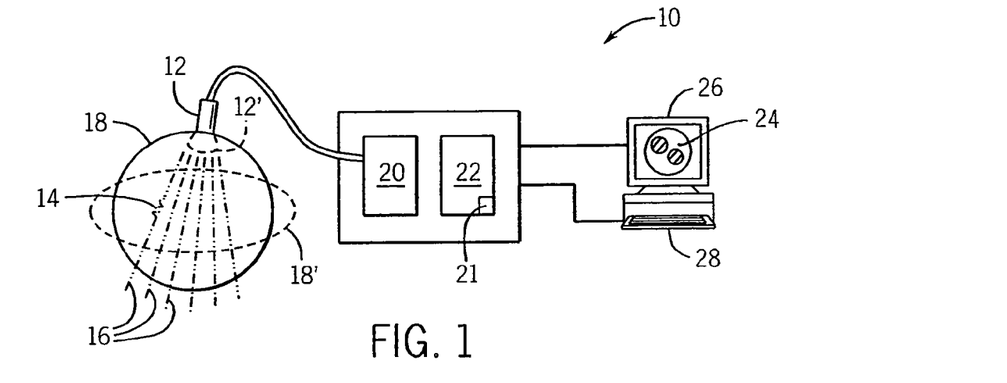
FIG. 1 is a block diagram of a sector scanning ultrasound machine as may be programmed to perform the present invention.

Referring now to FIG. 1, an ultrasonic imaging system 10 may provide an ultrasound transducer 12 receiving ultrasonic echo signals 14 along axial lines 16 through an imaged object such as tissue 18 of the patient. The axial lines 16 generally diverge from the ultrasonic transducer 12 to create a fan shaped beam collecting data from a sector shaped area.

The ultrasonic echo signals 14 may be received and processed by ultrasound acquisition circuitry 20 of a type well known in the art to provide radio frequency (RF) data to an elastography processor 22. A suitable ultrasonic imaging system 10 is a GE Vingmed Vivid 7 ultrasound system using a 2.5 MHz phased array transducer providing axial lines 16 over a 75° sector angle such as is commercially available from General Electric Company of the United States.

Another suitable ultrasonic imaging system 10 is a Siemens Antares SONOLINE ultrasound system using a C7F2 "fourSight" 4D Ultrasound mechanically rocked array transducer providing axial lines 16 over a 75° sector angle in the elevational direction such as is commercially available from Siemens of the United States. The array can be mechanically rotated in the elevational direction to scan different planes, each at a specified angle to the previously scanned plane. The maximum sector angle over which the array can be rotated (or wobbled) is approximately 75°.

As will be described in more detail below, the elastography processor 22 includes a program 21 of the present invention to produce elastographic images 24 that may be displayed on a display terminal 26. The elastographic images 24 depict one or more measures of stiffness of the tissue 18 of the patient. An input device 28 may communicate with the elastography processor 22 to allow the user to set or change various processing parameters used by the ultrasound acquisition circuitry 20 or the elastography processor 22.

Figure 2:
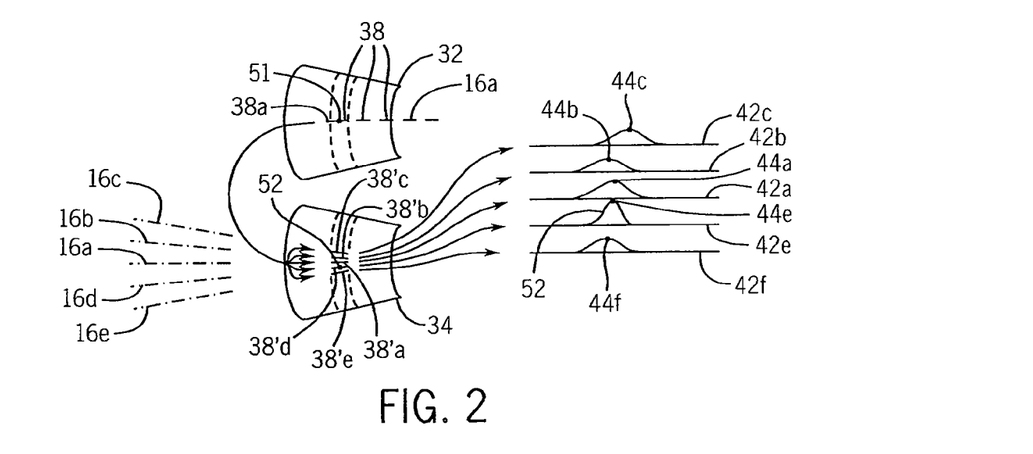
FIG. 2 is a simplified diagram of a pre-compression and post-compression sector image having a given pre-compression line segment correlated with multiple post-compression line segments displaced laterally from one another and showing the results of those correlations.
Figure 4:
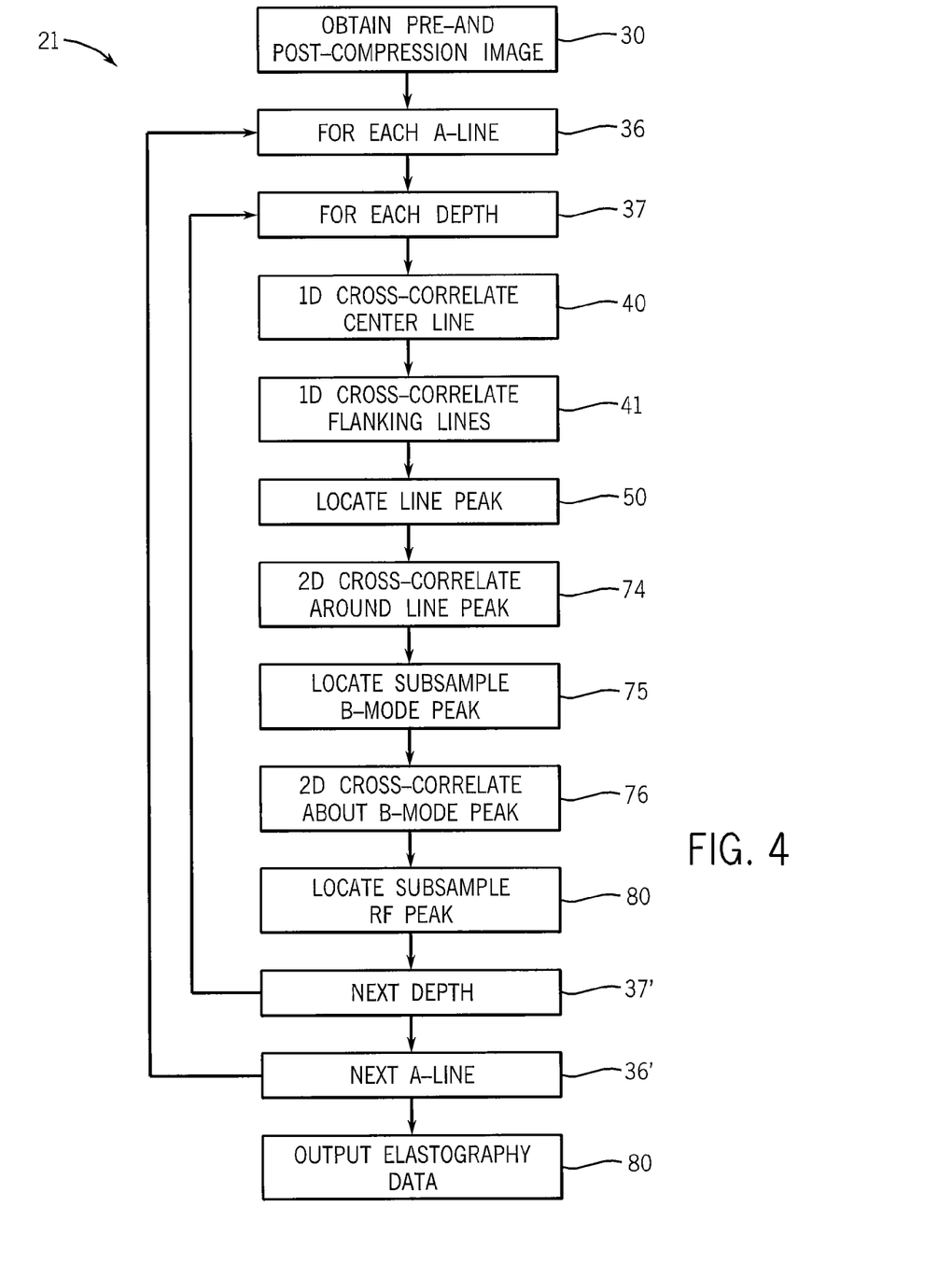
FIG. 4 is a flow chart of the steps implemented in the present invention as discussed with respect to FIGS. 2 and 3.

Referring now to FIGS. 1, 2 and 4, as indicated by process block 30 in FIG. 4, a pre-compression image 32 consisting of ultrasonic echo signals 14 over an area of the tissue 18 may be obtained using the transducer 12 lightly resting on the uncompressed tissue 18. By compressing the transducer 12 inward (as indicated by depicted transducer 12'), a post-compression image 34 of the compressed tissue 18' may be collected also consisting of ultrasonic echo signals 14 over substantially the same area as that covered by the pre-compression image 32. The images may for example provide for a 114 axial lines 16, each collecting radio frequency data to a 150 mm depth with a 20 MHz sampling rate.

Figure 5:
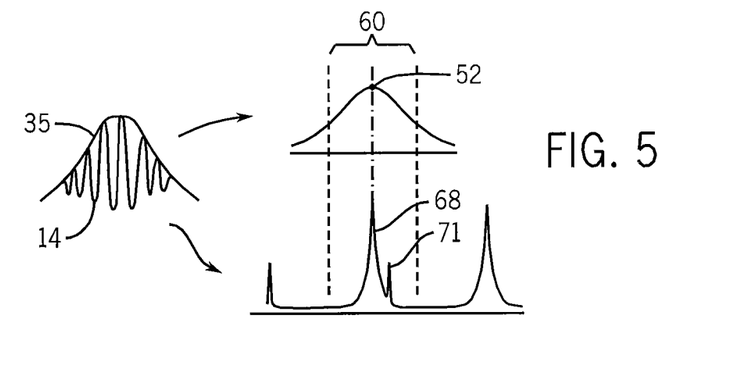
FIG. 5 is a plot of a B-mode signal and its underlying RF signal showing the use of the B-mode signal for a broad area correlation to be followed by correlation of the RF signal.

Referring momentarily to FIG. 5, the ultrasonic echo signals 14 may be processed by a program 21 to extract an envelope 35 indicating the amplitude of the ultrasonic echo signals 14 such as is termed B-mode data. The B-mode data may be used to generate a standard ultrasound image on the display terminal 26 by mapping the amplitude of the B-mode data to a brightness scale and will be used together with the RF data of the ultrasonic echo signals 14 for the elastographic processing.

As indicated by process blocks 36 and 37 of FIG. 4, the program 21 executing on the elastography processor 22 scans through the data taken on each axial line 16 of the pre-compression image 32 at each depth along each axial line 16 to determine an axial, lateral and/or elevational displacement of tissue 18 between the pre-compression image 32 and the post-compression image 34 at different points within the tissue 18.

Specifically and referring also to FIGS. 2 and 4, during that scanning process, a program executing on the elastography processor 22 scans through the pre-compression image 32 one axial line 16 at a time per a loop formed by process blocks 36 and 36', and on each given axial line, for example axial line 16a, scans through different successive segments 38 on that axial line 16a per a loop formed by process blocks 37 and 37'.

Within those loops, as indicated by process block 40, the B-mode data of each given segment 38 in the pre-compression image 32, for example segment 38a, is correlated to a corresponding line segment 38'a in the post-compression image 34, the line segment 38'a having essentially the same coordinates in the post-compression image 34 as segment 38a in the pre-compression image 32.

The result of these correlations between the data of line segment 38a and line segment 38'a produces a linear cross-correlation 42a having a peak correlation value 44a indicating a relative displacement finding maximum correlation and thus generally indicating the axial displacement of the tissue 18 between the pre-compression image 32 and the post-compression image 34.

As indicated by process block 41, the data of line segment 38a is then correlated to line segments 38'b, 38'c, 38'd, and 38'e having the same depth as line segment 38'a but flanking line segment 38'a and displaced laterally therefrom. Thus, segments 38'b and 38'c lie on axial lines 16b and 16c (being successively displaced axial lines to the right of axial line 16a viewed along the direction of the ultrasonic beam) and line segments 38'd and 38'e lie on axial lines 16d and 16e (being successively displaced axial lines to the left of axial lines 16a viewed along the direction of the ultrasound beam). Each of these correlations produces in turn correlation lines 42b-42f each having corresponding peak correlation values 44b-44f.

At process block 50, one correlation line 42a-42f having the highest peak correlation value 44a-44f is identified as the "line peak" 52 indicating both a depth or axial location (by the location of the peak correlation value 44 along the correlation line 42) and a lateral location (by the lateral location of the axial line 16 associated with the particular correlation line 42). The axial and lateral coordinates of the line peak 52 approximates the amount of displacement in two dimensions between tissue at a center point 51 centered on line segment 38a in the pre-compression image 32 and a corresponding tissue in the post-compression image 34.

Figure 7:
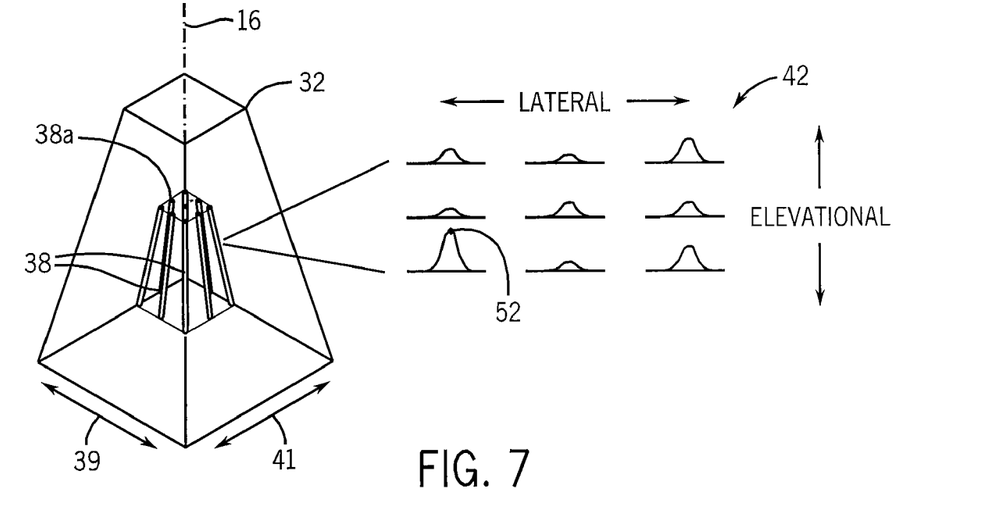
FIG. 7 is a figure similar to that of FIG. 2 showing determination of coarse displacement in the three-dimensional case.

Referring momentarily to FIG. 7, this process may be readily extended to three dimensions in which multiple line segments 38 are displaced both laterally 39 and elevationally 41 from a given line segment 38a and are investigated within a three-dimensional imaging volume 32. In this case, correlation lines 42 are collected both from all line segments 38 displaced laterally 39 and elevationally 41 and the line peak 52, identified as the highest peak correlation among all line correlations 42, provides a lateral, axial, and an elevational displacement.

Figure 3:
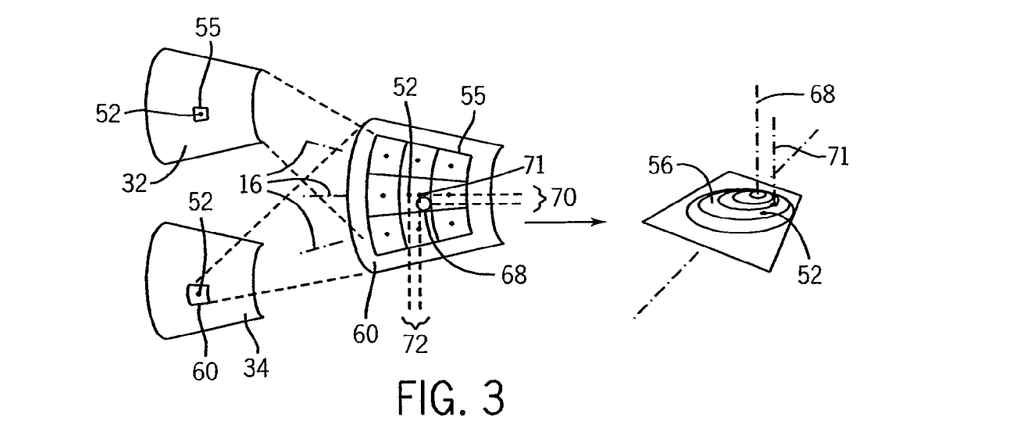
FIG. 3 is a simplified diagram of the process of two-dimensional correlation using a kernel centered on a coarse displacement determined in FIG. 2 and showing a perspective view of the resulting two-dimensional correlation.

Referring to FIG. 3, for the two-dimensional case of FIG. 2, this line peak 52 is then used to position a two-dimensional search window 60 in the post-compression image 34. A two-dimensional correlation kernel 55 takes B-mode data from the pre-compression image 32 in a sector shape corresponding to the local divergence of the axial lines 16 of that data. The correlation kernel 55 is preferably a 3×3 array of B-mode data arranged in a sector grid.

As represented by process block 74, the correlation kernel 55 is then cross-correlated to the data of the search window 60 in a two-dimensional correlation process. This two-dimensional correlation process is performed in a relatively small search window 60 (possible because of its accurate positioning using line peak 52) with a relatively limited amount of data and thus is extremely fast. The correlation process yields a correlation surface 56 having a subsample peak value 68 that will generally be displaced somewhat from the line peak 52 by a lateral amount 70 and axial amount 72. The identification of the subsample peak value 68 and its lateral and axial displacement with respect to center point 51 is performed as indicated by process block 75.

Figure 8:
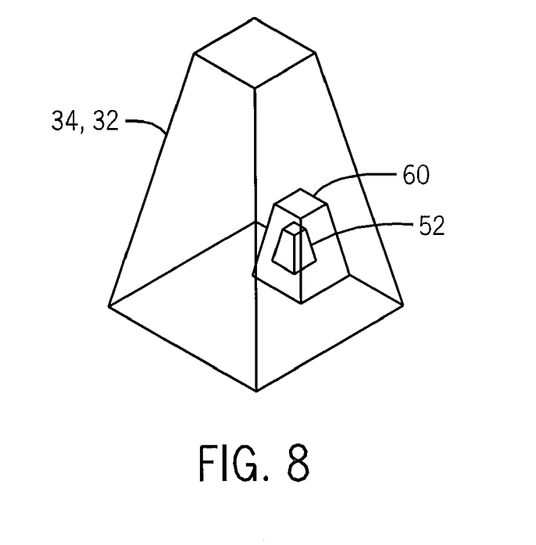
FIG. 8 is a figure similar to that of FIG. 3 showing selection of the search window in the three-dimensional case.

Referring now to FIG. 8, for the three dimensional case of FIG. 7, the line peak 52 is used to position a three-dimensional search area 60 in the post-compression image 34 which is correlated in either three dimensions with a convolution kernel of the pre-compression image 32. This convolution kernel analogously may be a 3×3×3 array of B-mode data arranged also in a three-dimensional sector grid conforming generally with the divergence of the ultrasound in two dimensions. The correlation surface, which is not readily depicted, provides more accurate subsample peak location in a manner that will be understood from the previous description. In yet a further embodiment, this correlation may be restricted to a plane (not shown) in either the lateral or elevational direction to reduce computations.

At process block 76, this subsample peak value 68 may be used in a manner similar to that of a line peak 52 for the second two or three-dimensional cross-correlation. In this second cross-correlation, the program may use the same or a smaller correlation kernel 55, but this time with a 3×3 array of RF data arranged in a sector grid. The higher resolution of the RF data (ultrasonic echo signals 14) provides for sharper correlation peaks and thus more precise displacement measurements.

Per process block 80, an RF subsample peak value 71 may then be determined analogous to subsample peak value 68 but having greater precision. This RF subsample peak value 71 provides a displacement amount with respect to center point 51 that may be used for the calculation of elastographic quantities associated with center point 51.

This process may then be repeated if desired for example with increasingly fine samples of the RF data.

After the RF subsample peak value 71 has been determined for a particular line segment 38a, the next line segment 38 is analyzed to determine a corresponding RF subsample peak value 71 using the same process per the loop established by process block 37 and 37'. Once the line segments 38 of a full line axial line 16 have been analyzed, the next axial line 16 is analyzed per the loop established by process blocks 36 and 36'.

At the completion of the loops defined by process blocks 36 and 37, strain data, for example, in an elastographic image may be output per process block 80.

Referring now to FIG. 5, a typical line peak 52 for B-mode data will be associated with a relatively broad maximum that will define a search window 60 unambiguously identifying a single subsample peak value 68 or 71 (based on B-mode or RF data), the search window 60 preventing cross-correlation artifacts where other correlation peaks in the two-dimensional cross-correlation are wrongly identified.

Figure 6:
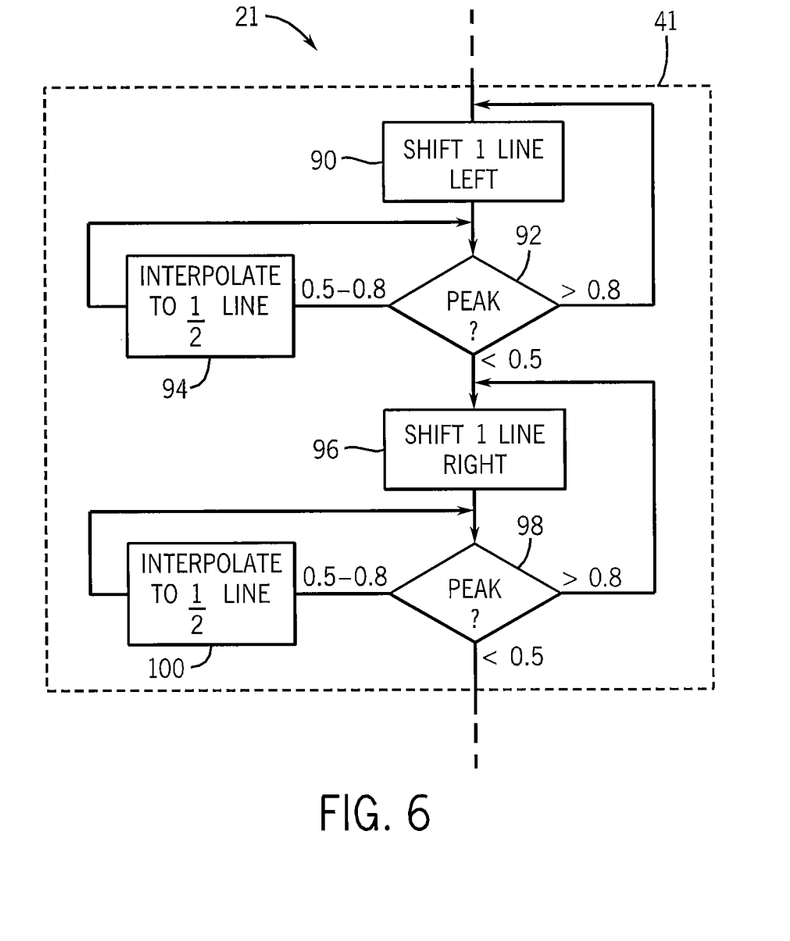
FIG. 6 is a detailed flow chart of an alternative embodiment of one process block of FIG. 4 showing the use of an adaptive cross-correlation to reduce processing time.

Referring now to FIG. 6, the step of process block 41 in which a given segment 38 in the pre-compression image 32 is cross-correlated to multiple corresponding segments 38' in the post-compression image 34, can be made more efficient by adaptively varying the number of flanking adjacent segments 38' that will be cross-correlated based on a running analysis of the change in the height of peak correlation value 44 for each successive adjacent segments 38'.

Thus, referring to FIGS. 2 and 6, in one embodiment of the invention, after the data of segment 38a in the pre-compression image 32 is correlated to the data of segment 38'a in the post-compression image 34, the program 21 moves one axial line 16 to the left per process block 90. At decision block 92, a cross-correlation between data segments (in this case, data segment 38a and data segment 38'b) is performed. The resulting peak correlation value (44b) is compared to the previous peak correlation value (in this case, peak correlation value 44a between segment 38a and 38'a). If the latest peak correlation value 44b is greater than or equal to 0.8 times (80% of) the peak correlation value 44a, the program 21 loops back to process block 90 and shifts left another axial line 16 to the left (to data segment 38'c) as long as the total number of leftward shifts is less than a predetermined amount (for example 3).

If at decision block 92, the peak correlation value 44b is between 0.5-0.8 times (50% and 80% of) the peak correlation value 44a, then a new interpolated line will be calculated between previously analyzed line (in this case data segment 38b) and the latest line (in this case data segment 38c) as indicated by process block 94. The peak correlation value of this interpolated line is again analyzed at decision block 92. Only one line may be interpolated before this loop is exited.

If at decision block 92, the peak correlation value 44b is less than 50% of the initial peak correlation value 44a then no further flanking lines are analyzed and the program 21 proceeds to process block 96.

At process block 96 similar steps are taken in determining how many flanking data segments 38 to analyze to the right of the data segment 38'a. In this respect, process block 96 corresponds generally to process block 90 yet with a rightward shift. Process block 98 corresponds generally to decision block 92 and may lead to process block 100 (corresponding generally to process block 94) or may provide for termination of block 41 when the peak is less than 50% of the maximum.

This process of dynamically analyzing the peak correlation values 44 eliminates the need to analyze laterally or elevationally displaced data segments when the correlation is decreasing and thus it is unlikely that additional flanking data segments 38 will yield a line peak 52. This process also allows interpolation to improve the lateral resolution of this coarse estimate of process block 41 otherwise governed by the spacing between axial lines 16 which is generally coarser than the sample rate along axial lines 16.

It is specifically intended that the present invention not be limited to the embodiments and illustrations contained herein and the claims should be understood to include modified forms of those embodiments including portions of the embodiments and combinations of elements of different embodiments as come within the scope of the following claims.

We claim:

1. A method of multidimensional strain imaging comprising the steps of:
    (a) obtaining a pre-compression and post-compression ultrasonic data set of an imaged object composed of measurements along multiple laterally spaced and mutually non-intersecting axial lines through the imaged object by ultrasound propagating along the multiple axial lines;
    (b) using a programmed electronic computer executing a program stored in non-transient medium, and receiving the ultrasonic data sets, for each given axial line in the pre-compression ultrasonic data set and for each depth along each given axial line:
        (i) performing a one dimensional correlation of measurements of the given axial line at a range of depths with measurements at corresponding depths of a corresponding axial line and laterally adjacent axial lines to the corresponding axial line in the post-compression ultrasonic data set;
        (ii) identifying one of the corresponding axial line and adjacent axial lines in the post-compression ultrasonic data set having maximum correlation with the given axial line and identifying a line peak based on an axial depth and lateral position of that maximum correlation as a line peak;
        (iii) performing a local multidimensional correlation between the pre-compression and post-compression ultrasonic data sets at points determined from the line peak about the line peak to determine a subsample peak;
        (iv) determining a displacement vector using the subsample peak;
    (c) displaying multidimensional strain data based on multiple displacement vectors determined from corresponding subsample peaks for multiple axial lines at a plurality of locations in the imaged object.

2. The method of claim 1 wherein the adjacent axial lines are laterally displaced from the corresponding axial line, the lateral direction being perpendicular to the axial lines, and the output strain data is two-dimensional strain data.

3. The method of claim 1 wherein the adjacent axial lines are laterally and elevationally displaced from the corresponding axial line, the lateral and elevational directions being perpendicular to each other and to the axial lines and wherein the output is three-dimensional strain data.

4. The method of claim 3 where the multidimensional correlation is a two dimensional correlation in a plane including the line peak.

5. The method of claim 3 where the multidimensional correlation is a three dimensional correlation in volume including the line peak.

6. The method of claim 1 wherein the multiple axial lines diverge through the imaged object and wherein the multidimensional correlation is performed on a sector grid conforming to a divergence of the axial lines near the line peak.

7. The method of claim 1 wherein the one dimensional correlation of step (i) is performed on B-mode data.

8. The method of claim 1 wherein step (iii) comprises:
    (a) performing a multidimensional correlation between the pre-compression and post-compression ultrasonic data sets at points about the line peak to determine a coarse subsample peak; and
    (b) performing a multidimensional correlation between the pre-compression and post-compression ultrasonic data sets at points about the coarse subsample peak to determine the subsample peak, the subsample peak providing finer resolution of displacement than the coarse subsample peak.

9. The method of claim 5 wherein the coarse subsample peak uses B-mode data for the local multidimensional correlation and the subsample peak uses RF data for the local multidimensional correlation.

10. The method of claim 5 wherein the multiple axial lines diverge through the imaged object and wherein the local multidimensional correlations are performed on a sector grid conforming to the divergence of the axial lines near the line peak.

11. The method of claim 1 wherein the number of adjacent axial lines varies according to a relative change in peak correlation with respect to the peak correlation of the corresponding line.

12. The method of claim 1 wherein at least one adjacent axial line is an interpolated line between measurements of two axial lines.

13. The method of claim 1 wherein at least one laterally adjacent axial line is interpolated between measurements of two axial lines when an axial line of the two axial lines that is furthest from the corresponding axial line has a predetermined lower maximum correlation.

14. A program for multi-dimensional strain imaging, the program embodied in a non-transitory, tangible computer readable storage medium for execution by an electronic computer to perform the steps of:
(a) obtaining a pre-compression and post-compression ultrasonic data set of an imaged object composed of measurements along multiple laterally spaced and mutually non-intersecting axial lines through the imaged object by ultrasound propagating along the multiple axial lines;
(b) for each given axial line in the pre-compression ultrasonic data set and for each depth along each given axial line:
(i) performing a one dimensional correlation of measurements of the given axial line at a range of depths with measurements at corresponding depths of a corresponding axial line and laterally adjacent axial lines to the corresponding axial line in the post-compression ultrasonic data set;
(ii) identifying a line of the corresponding axial line and adjacent axial lines in the post-compression ultrasonic data set having maximum correlation and identifying the axial depth of that maximum correlation on that identified one of the corresponding axial lines to determine as a line peak;
(iii) performing a multidimensional correlation between the pre-compression and post-compression ultrasonic data sets at points determined from the line peak about the line peak to determine a subsample peak;
(iv) determining a displacement using the subsample peak;
(c) displaying multidimensional strain data based on multiple displacements determined from corresponding subsample peaks for multiple axial lines at a plurality of locations in the imaged object.

15. The program of claim 14 wherein the adjacent axial lines are laterally displaced from the corresponding axial line and the output strain data is two-dimensional strain data.

16. The program of claim 14 wherein the adjacent axial lines are laterally and elevationally displaced from the corresponding axial line, the lateral and elevational directions being perpendicular to each other and to the axial lines and wherein the output is three-dimensional strain data.

17. The program of claim 16 where the multidimensional correlation is a two dimensional correlation in a plane including the line peak.

18. The program of claim 16 where the multidimensional correlation is a three dimensional correlation in a volume including the line peak.

19. The program of claim 14 wherein the multiple axial lines diverge through the imaged object and wherein the multidimensional correlation is performed on a sector grid conforming to a divergence of the axial lines near the line peak.

20. The program of claim 14 wherein the linear correlation of step (i) is performed on B-mode data.

21. The program of claim 14 wherein step (iii) comprises:
(a) performing a multidimensional correlation between the pre-compression and post-compression ultrasonic data sets at points about the line peak to determine a coarse subsample peak; and
(b) performing a local multidimensional correlation between the pre-compression and post-compression ultrasonic data sets at points about the coarse subsample peak to determine the subsample peak, the subsample peak providing finer resolution of displacement than the coarse subsample peak.

22. The program of claim 21 wherein the coarse subsample peak uses B-mode data for the local multidimensional correlation and the subsample peak uses RF data for the local multidimensional correlation.

23. The program of claim 21 wherein the multiple axial lines diverge through the imaged object and wherein the local multidimensional correlations are performed on a sector grid conforming to a divergence of the multidimensional lines near the line peak.

24. The program of claim 14 wherein the number of laterally adjacent axial lines varies according to a relative change in peak correlation with respect to the peak correlation of the corresponding line.

25. The program of claim 14 wherein at least one laterally adjacent axial line is an interpolated line between measurements of two axial lines when an axial line of the two axial lines that is furthest from the corresponding axial line has a predetermined lower maximum correlation.

* * * * *